United States Patent
Weng et al.

(10) Patent No.: US 9,398,926 B2
(45) Date of Patent: Jul. 26, 2016

(54) INTERSPINOUS STABILIZATION DEVICE

(75) Inventors: Yu-Shi Weng, Pingtung (TW); Yi-Hung Lin, Jhubei (TW); Ya-Jen Yu, Taipei (TW); Shan-Chang Chueh, Taipei (TW); I-Ching Wu, Solana Beach, CA (US); Chris I. Huang, Hercules, CA (US)

(73) Assignee: Industrial Technology Research Institute, Hsinchu (TW)

( * ) Notice: Subject to any disclaimer, the term of this patent is extended or adjusted under 35 U.S.C. 154(b) by 1762 days.

(21) Appl. No.: 12/436,010

(22) Filed: May 5, 2009

(65) Prior Publication Data

US 2010/0076560 A1 Mar. 25, 2010

Related U.S. Application Data

(60) Provisional application No. 61/050,441, filed on May 5, 2008.

(51) Int. Cl.
*A61F 2/44* (2006.01)
*A61B 17/70* (2006.01)

(52) U.S. Cl.
CPC ......... *A61B 17/7062* (2013.01); *A61B 17/7065* (2013.01); *A61F 2/44* (2013.01); *A61F 2/4405* (2013.01)

(58) Field of Classification Search
USPC ............................................ 623/17.16, 17.11
See application file for complete search history.

(56) References Cited

U.S. PATENT DOCUMENTS

| | | | |
|---|---|---|---|
| 4,743,256 A * | 5/1988 | Brantigan | 128/898 |
| 5,496,318 A * | 3/1996 | Howland et al. | 606/249 |
| 5,609,634 A | 3/1997 | Voydeville | |
| 5,609,635 A | 3/1997 | Michelson | |
| 5,645,599 A * | 7/1997 | Samani | 623/17.16 |
| 6,068,630 A | 5/2000 | Zucherman et al. | |
| 6,358,254 B1 | 3/2002 | Anderson | |
| 6,440,169 B1 | 8/2002 | Elberg et al. | |
| 6,582,433 B2 | 6/2003 | Yun | |
| 6,626,944 B1 | 9/2003 | Taylor | |
| 6,966,929 B2 * | 11/2005 | Mitchell | 623/17.11 |
| 7,029,473 B2 * | 4/2006 | Zucherman et al. | 606/249 |
| 7,029,475 B2 | 4/2006 | Panjabi | |
| 7,048,736 B2 * | 5/2006 | Robinson et al. | 606/86 B |
| 7,083,649 B2 * | 8/2006 | Zucherman et al. | 623/17.11 |
| 7,087,084 B2 * | 8/2006 | Reiley | 623/17.11 |
| 7,585,316 B2 * | 9/2009 | Trieu | 606/279 |
| 2004/0243239 A1 * | 12/2004 | Taylor | A61B 17/7062 623/17.13 |
| 2005/0261768 A1 * | 11/2005 | Trieu | 623/17.11 |
| 2005/0277930 A1 * | 12/2005 | Parsons | 606/61 |
| 2006/0106397 A1 * | 5/2006 | Lins | 606/90 |
| 2006/0247640 A1 * | 11/2006 | Blackwell et al. | 606/71 |
| 2007/0010813 A1 * | 1/2007 | Zucherman et al. | 606/61 |
| 2007/0049935 A1 * | 3/2007 | Edidin et al. | 606/61 |
| 2007/0191833 A1 * | 8/2007 | Bruneau et al. | 606/61 |
| 2007/0191837 A1 * | 8/2007 | Trieu | 606/61 |

* cited by examiner

*Primary Examiner* — Jacqueline Woznicki
(74) *Attorney, Agent, or Firm* — Cesari and McKenna LLP

(57) ABSTRACT

An interspinous stabilization device includes: (1) a supporting member with a top surface and a bottom surface both being configured to engage spinous processes; (2) two side members connected to the supporting member; (3) a fastener attached to the side members; and optionally (4) two extendable arms each secured on one of the side members.

19 Claims, 8 Drawing Sheets

INTERSPINOUS STABILIZATION DEVICE

CROSS-REFERENCE TO RELATED APPLICATIONS

This application claims the benefit of the filing date of U.S. Application No. 61/050,441, which was filed May 5, 2008. This prior application is hereby incorporated by reference herein in its entirety.

TECHNICAL FIELD

This invention relates to an interspinous stabilization device.

BACKGROUND

Spinal stenosis is an abnormal narrowing of the spinal canal, which compresses the spinal cord and lateral nerves, resulting in cramping, pain or numbness in a patient's legs, back, neck, shoulders or arms. While it may affect young patients due to developmental abnormalities, spinal stenosis is a common degenerative condition that afflicts aged people.

Most advanced cases of spinal stenosis require surgical treatment, while mild cases can be treated by non-surgical means, such as physical therapy or pain management. To date, the most common surgical treatment is spinal fusion, which is performed by placing a bone graft, bone substitute, and/or a non-natural instrument such as a metal rod between the vertebrae being fused. Spinal fusion often limits the activity of the vertebrae being fused, and it may cause damage to the vertebrae or nearby tissues. Because of these risks, non-fusion techniques that aim to stabilize the affected vertebrae but still maintain their function have been developed. These techniques include the implantation of artificial discs, nucleus replacement, annular repair, and dynamic stabilization systems. However, most of these techniques are highly invasive, requiring the removal of bone, muscle or ligament, or are difficult to perform. Thus, there is still a need for simple, minimally invasive non-fusion techniques for treating spinal stenosis and similar conditions.

SUMMARY

The present invention relates to an interspinous stabilization device that can be used (e.g., surgically inserted or implanted) between two adjacent spinous processes of the vertebral column to relieve discomfort associated with certain spinal conditions and disorders.

In one aspect, an implementation of the device includes a supporting member connected to two side members to which a fastener (e.g., a hook-typed fastener, a clip, or a male-female-type connector) can attach. The supporting member has a top surface and a bottom surface, both of which are designed to engage adjacent spinous processes. The size and shape of the top and bottom surfaces can be configured to better accommodate a portion of a spinous process of a similar size and complementary shape. For example, the top surface and/or the bottom surface can be recessed in the shape of an arc, a "U" or a semicircle to accommodate a spinous process having a surface that protrudes in the shape of an arc, a "U" or a semicircle. The top surface of the supporting member would support (e.g., abut or receive) a lower surface of a spinous process of the vertebrae above the supporting member, and the bottom surface of the supporting member would support an upper surface of a spinous process of the vertebrae below the supporting member.

The two side members can be ladder-shaped, and can extend away from the supporting member in parallel. Alternatively, or when the fastener is fastened, the two side members can extend away from the supporting member at converging angles so the overall shape of the device is wedge-shaped (or becomes wedge-shaped when the fastener is fastened). The height of the side members can vary along their length. For example, the height of the side members where the side members are in contact with the supporting member can be greater than the height of the side members distal to the supporting member, where a fastener may be attached. Thus, the side members, in a perspective view, can be pie- or wedge-shaped. Upon implantation, the thinner edge of the wedge would extend toward the vertebral body. We may refer to the side members as "left" and "right" side members.

In another aspect, the above-described implementation further includes two extendable arms. The first extendable arm is secured to the first side member, and the second extendable arm is secured to the second side member. The arms can be secured to the side members on surfaces that are exterior surfaces of the device. The arms can vary in shape and may be extendible such that the length of an arm can vary from its point of attachment to the device. The arms can be bar-like, tubular, conical, X-shaped, or wing-shaped, and each arm can be secured to one of the side members through a connector (e.g., a pin, a tack, a screw, or the like) in a manner such that the arms can be rotated around the connector allowing their distal ends to be brought into contact with a portion of a spinous process. Deploying the arms can add additional stability to the spine. Extendible arms may facilitate the initial phase of implantation.

Also within the scope of this invention is a method for maintaining an anatomical distance between two adjacent spinous processes with the above-described device. More specifically, the present device can be implanted into a subject by a surgical procedure through, for example, a posterior approach. The method can include a step of identifying a patient in need of treatment, and that patient can be a human being.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

FIG. 8A depicts an interspinous stabilization device clipped onto a spinal process or ligaments in a closed state.

FIG. 8B depicts an interspinous stabilization device clipped onto a spinal process or ligaments with the arms open ("open wing").

Other features and advantages of the interspinous stabilization device will appear in the following description and are referenced in the attached drawings, which illustrate implementations of the device by way of non-limiting examples.

DETAILED DESCRIPTION

Figure 1:
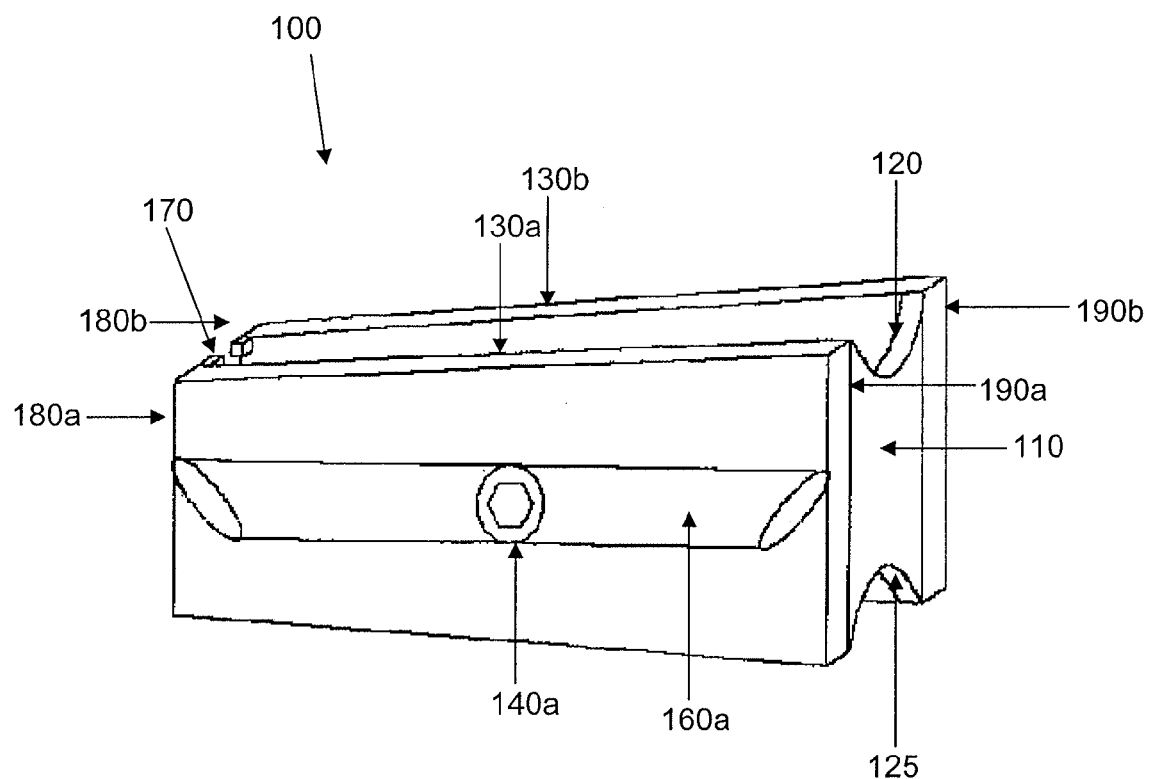
FIG. 1 depicts a perspective view of an implementation of an interspinous stabilization device.
Figure 2:
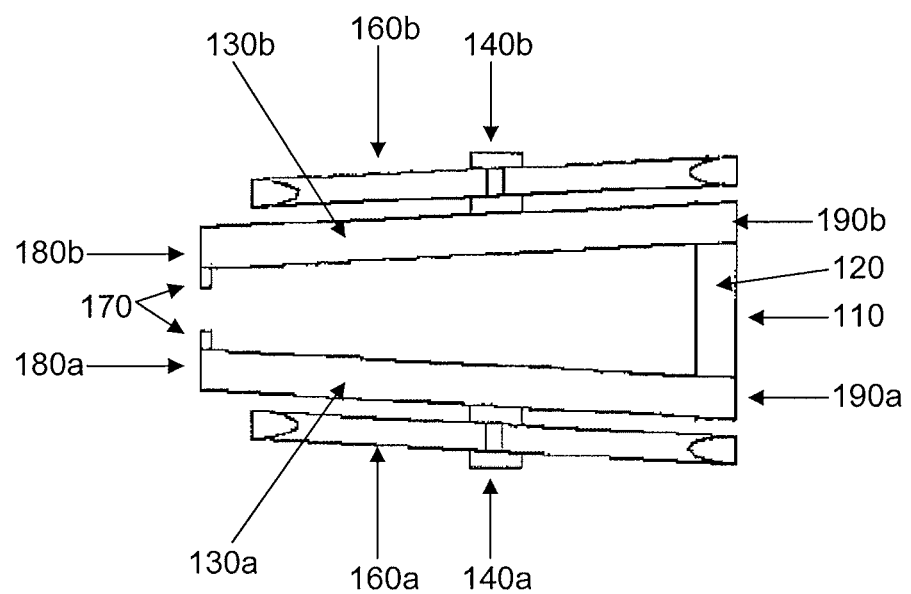
FIG. 2 depicts a top view of an implementation of the interspinous stabilization device.

Referring to FIG. 1 and FIG. 2, an implementation of the interspinous stabilization device 100 includes a supporting member 110 connected to two side members, 130a and 130b, to which a fastener 170 is attached.

The supporting member 110 defines a top surface 120 and a bottom surface 125, both of which are designed to facilitate physical interact with adjacent spinous processes. The top surface 120 articulates with the spinous process of the vertebrae above the device (i.e., the vertebrae of the adjacent pair that is closer to the patient's head), and the bottom surface 125 articulates with the spinous process of the vertebrae below the device (i.e., the vertebrae of the adjacent pair that is further from the patient's head).

Each side member has a first end and a second end. The side member 130a has a first end 190a and a second end 180a, and the side member 130b has a first end 190b and a second end 180b.

Both of the first ends 190a and 190b are longer than the second ends 180a and 180b. Thus, the height of the side members 130a and 130b gradually reduces from the former to the latter, and the device 100 displays a wedge shape. The two side members 130a and 130b are not parallel to each other. As a result, the distance between the two first ends 190a and 190b can be greater than the distance between the two second ends 180a and 180b. One or more of the outer corners or edges of each of side members 130a and 130b can be curved or otherwise shaped to eliminate sharp corners.

Referring to FIG. 1 and FIG. 2, the fastener 170 is attached to the second ends 180a and 180b of the two side members 130a and 130b. The fastener 170 can be of any type of fastener that secures 130a to 130b. For example, the fastener can be a hook-type fastener, a clip, or a fastener containing male-female connectors. The fastener can be secured to either spinal processes or interspinous process ligaments.

In other aspects, the device can be configured to receive a fastener that is not initially an integral part of the device. For example, the second ends 180a and 180b can include holes or hooks through which, or by which, a fastener (e.g., a clip, suture, screw, or nut and bolt) can be secured to the device after it has been positioned. The holes and/or hooks can vary in number (e.g., there may be one, two, three or more holes and/or hooks in each of second ends 180a and 180b) and in their location along the side members 130a and 130b in order to provide the surgeon with options as to where the fastener(s) would be placed and which types of fastener(s) may be used.

Referring to FIG. 1 and FIG. 2, arms 160a and 160b can be attached to the outer surface of one or both of opposing side members 130a and 130b by connectors 140a and 140b. The arms 160a and 160b are attached in a manner that allows one to rotate the arms around the connectors 140a and 140b and thereby bring a distal end of arms 160a and 160b into contact with a spinous process of an adjacent vertebrae. The connectors 140a and 140b can be, for example, screws, tacks, or pins. The arm can be of many shapes. For example, the arms can be bar-like (with or without smoothened edges), tube-like, conical, X-shaped, or wing-shaped. The arm can have multiple components and can be configured to be extendable. For example, the arm can unfold around a joint to elongate or otherwise extend the arm. Alternatively, the arm can be configured such that one portion initially lies inside another and extension is achieved by a telescoping mechanism. Where the arms are extendible, a locking device may be included to stabilize the arms in the extended position.

Figure 3:
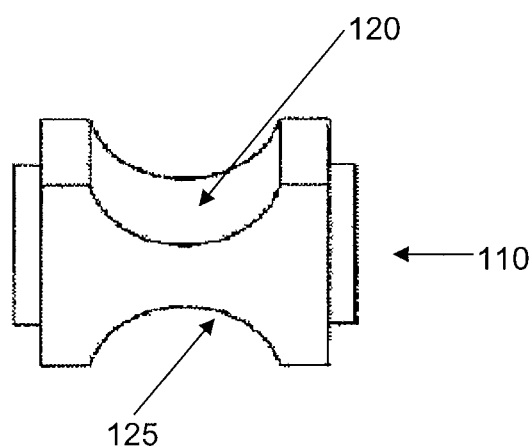
FIG. 3 depicts a perspective view of an implementation of the supporting member of the interspinous stabilization device.

Referring to FIG. 3, the supporting member 110 defines a top surface 120 and a bottom surface 125, both top and bottom surfaces being designed to physically interact with adjacent spinous processes.

Figure 4:
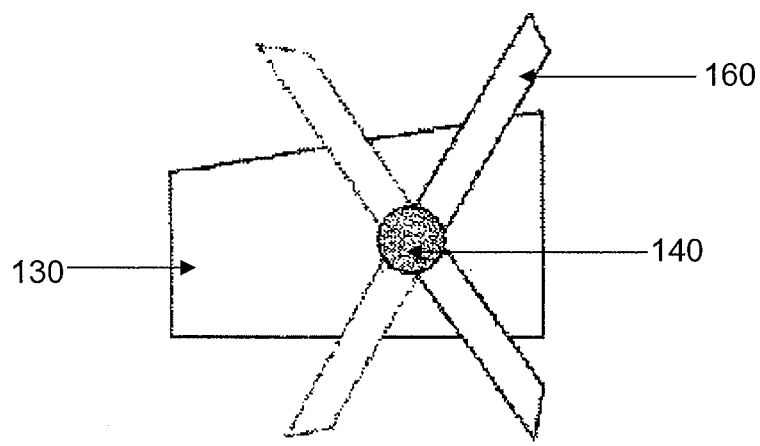
FIG. 4 depicts a side view of an extendable arm of an implementation of the interspinous stabilization device.

Referring to FIG. 4 an arm 160 can be attached to the outer surface of one or both of opposing side members 130 by a connector 140. More specifically, the center or substantial center of the X-shaped arm 160 is secured to side member 130 by the connector 140. The arm 160 is attached in a manner that allows one to rotate the arm around the connector 140, which can be a screw, a tack, or a pin. As noted, the shape of the arm can vary, and the arm can have multiple components that allow its extension and/or subsequent stabilization.

Figure 5B:
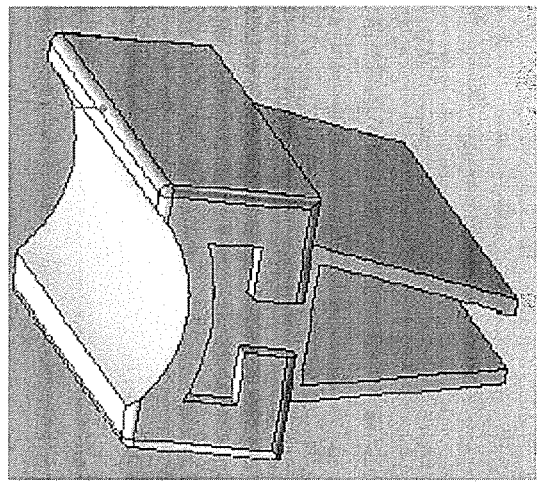
FIG. 5B depicts an implementation of the same interspinous stabilization device as pictured in FIG. 5A with the components assembled.
Figure 5A:
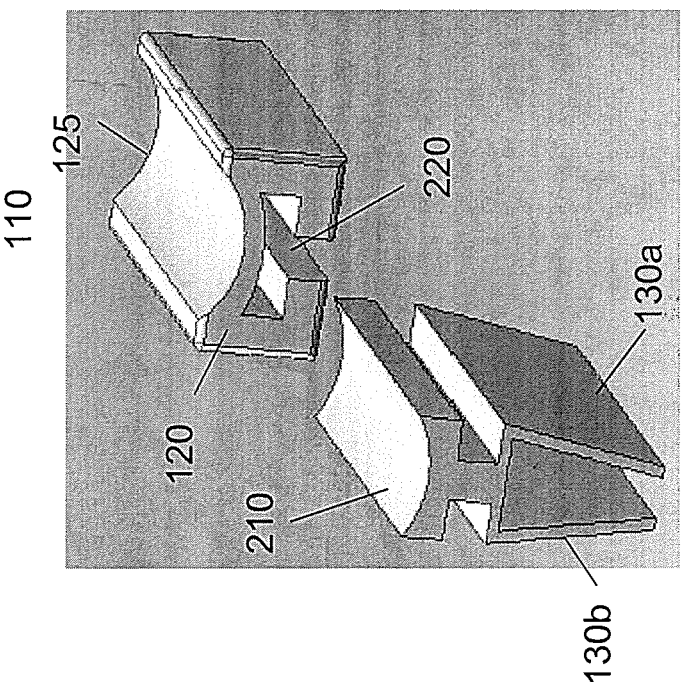
FIG. 5A depicts an implementation of an interspinous stabilization device with detachable components with the components disassembled.

Referring to FIGS. 5A and 5B side members 130a and 130b can be part of a contiguous unit 200, which has an integral male-type fastener 210 that connects to a corresponding female-type fastener 220 on a supporting member 110 which has a top surface 120 and a bottom surface 125, both of which are designed to facilitate physical interaction with adjacent spinous processes. The top surface 120 articulates with the spinous process of the vertebrae above the device (i.e., the vertebrae of the adjacent pair that is closer to the patient's head), and the bottom surface 125 articulates with the spinous process of the vertebrae below the device (i.e., the vertebrae of the adjacent pair that is further from the patient's head).

Figure 6A:
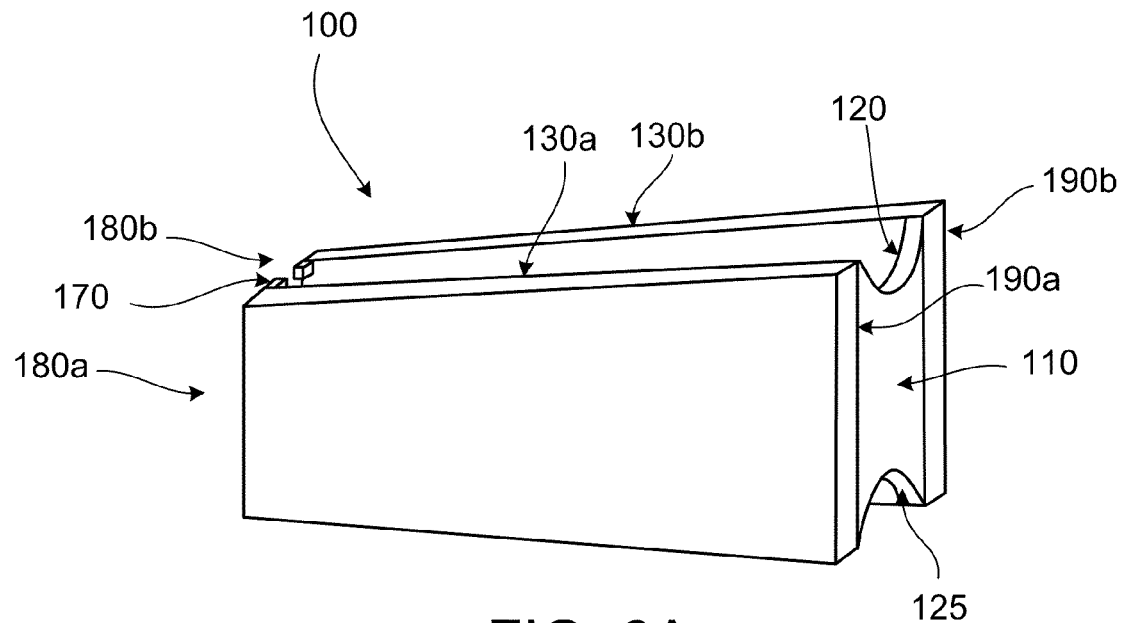
FIG. 6A depicts a perspective view of an interspinous stabilization device configured for use without arms.
Figure 6B:
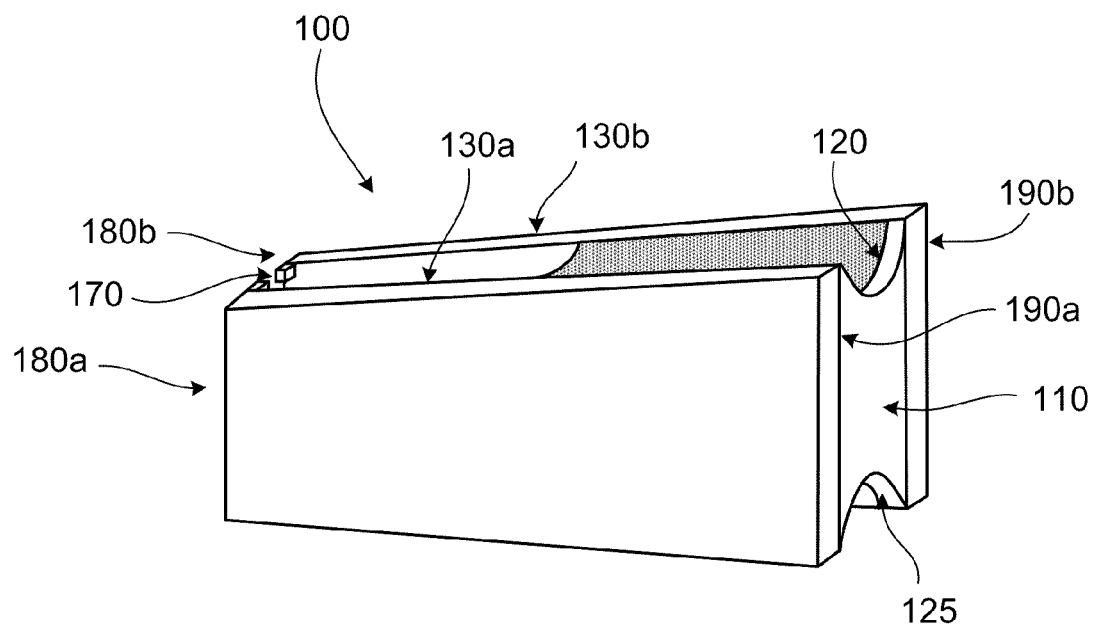
FIG. 6B depicts a perspective view of an interspinous stabilization device with extended upper and lower surfaces to provide increased areas of contact with spinal processes.

Referring to FIG. 6A, an interspinous stabilization device without optional arms (e.g., 160a and 160b). The second ends 180a, 180b can clip onto either a spinal process or interspinous process ligament. The top and bottom surfaces 120, 125 can be extended toward the second ends 180a, 180b, to provide a larger area of contact between the upper and lower surfaces of the device and a spinal process or ligament. See the shaded region extending from top surface 120 in FIG. 6B.

Figure 7A:
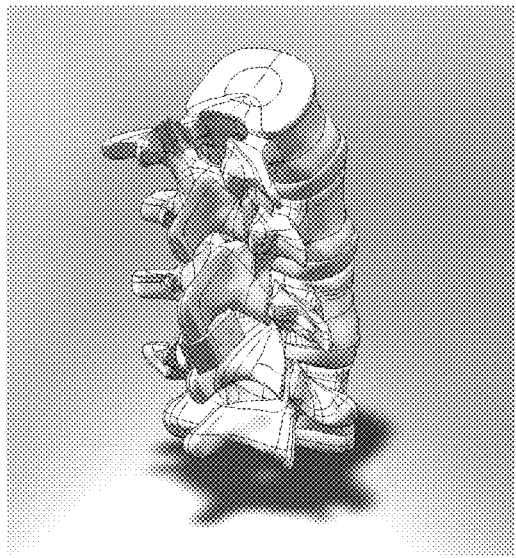
FIGS. 7A-7C depict an interspinous stabilization device without arms implanted in the spinal column and clipped onto spinal ligaments (FIGS. 7A and 7B) or spinal processes (FIG. 7C). The implant/device is first inserted in an opened state.
Figure 7B:
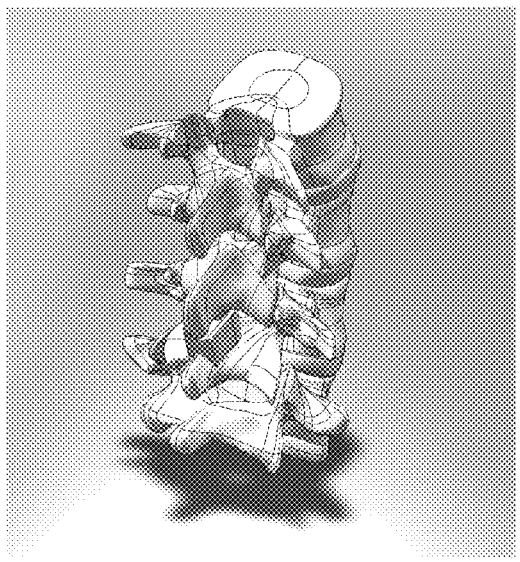
Figure 7C:
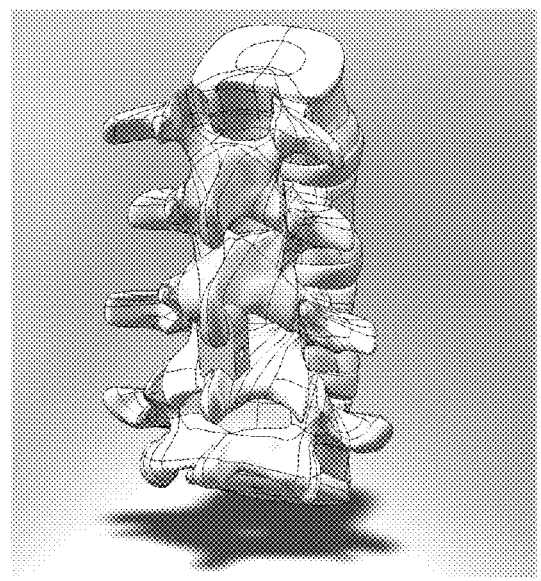

Referring to FIGS. 7A-7C, the interspinous stabilization device can be deployed without arms by clipping the device to a ligament or other spinal process.

Figure 8A:
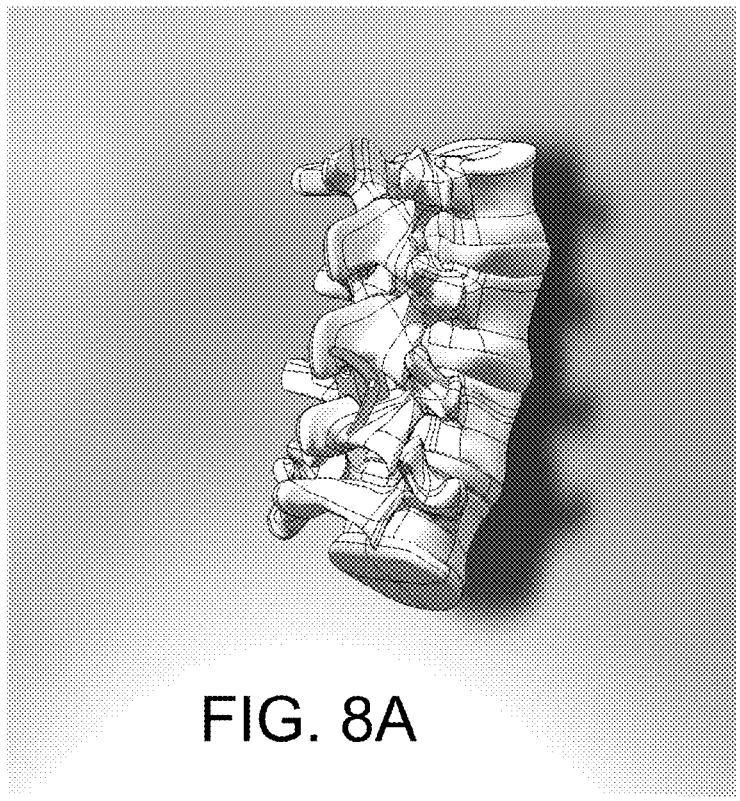
FIGS. 8A and 8B depict an interspinous stabilization device with arms implanted in the spinal column.
Figure 8B:
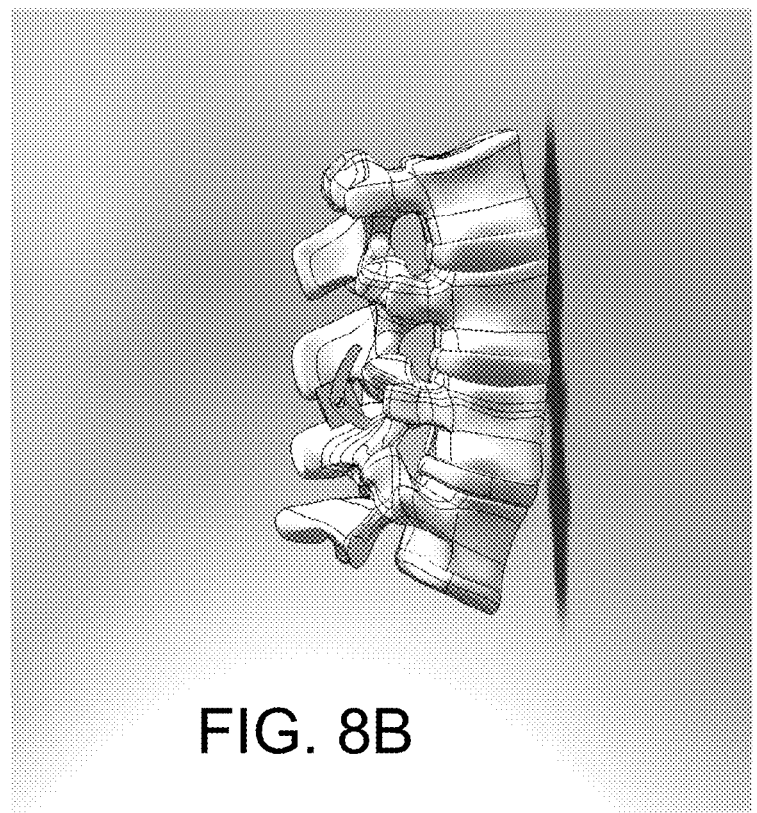

Referring to FIGS. 8A and 8B, the arms of the interspinous stabilization device can function in a closed (FIG. 8A) or open (FIG. 8B) state.

The interspinous stabilization device can be made of any type of biocompatible material. Suitable biocompatible materials include metals (e.g., stainless steel and titanium), ceramics, plastics, elastics, including rubber, polymers, composite materials, or any combination thereof. Biocompatible materials are materials that do not cause toxic or injurious effects in a subject, including human patients, in which the implementation is implanted. The materials can be porous, multi-layered, coiled, elastic or damping.

The stabilization device can be implanted between two adjacent spinous processes of two neighboring vertebrae. Once implanted, the supporting member 110 of the device engages the adjacent spinous processes to support them and maintain the anatomical height between them. The fastener 170 connects the two side members of the device to stabilize the position of the device between vertebrae. One or more arms 160, although not required for every implementation, help stabilize the position of the device relative to the vertebrae.

When implanted, the device can provide one or more of the following benefits. It may: (1) control the extent to which the spinal column is able to move (e.g., move backward), thus reducing the mechanical force on the posterior annulus accompanied with spinal column movement; (2) stabilize neighboring vertebrae with respect to one another; and (3) maintain the anatomical distance between neighboring vertebrae, thus expanding the spinal canal to avoid compressing the spinal cord and lateral nerves. As a result, the present device can relieve pain associated with spinal stenosis or other spinal disorders in which the spinal cord and lateral nerves are compressed due to the narrowing of the spinal canal.

The interspinous stabilization device described here is useful in the prevention or treatment of various spine and back disorders including, but not limited to, spinal stenosis, spinal disc herniation, scoliosis, facet osteoarthritis, lower back pain, spondylolisthesis, disc degeneration disease and facet arthropathy. Although the present device is not limited to one that provides a benefit by any particular mechanism, surgical implantation of the interspinous stabilization device described herein may be useful in maintaining the appropriate anatomical height of spinous processes in a subject.

These conditions may arise in an individual due to injury or aging and can impose significant restrictions on physical activity. For example, spinal stenosis is related to degeneration in the spine and usually becomes significant in individuals in their fifties and onwards. As individuals age, the spinal discs become less spongy and less fluid filled, resulting in reduced spinal disc height and bulging of the hardened disc into the spinal canal. The bones and ligaments of the spinal facet joints can thicken and enlarge due, for example, to arthritis, and push into the spinal canal. These changes cause narrowing of the lumbar spinal canal, resulting in spinal stenosis.

Individuals in need of treatment will present symptoms such as lower back pain, leg pain, numbness, weakness, and tingling with activity. Pain may be relieved with sitting. Clinical diagnosis of the disorders described here focuses on determining the source of an individual's pain by synthesizing findings from a review of the individual's medical history, a complete physical exam, and, if appropriate, the results of one or more diagnostic tests. The medical history can include a description of when the pain or symptoms occur, a description of how the pain feels, and what activities, positions, and treatments alleviate the pain. A physical exam can include testing of nerve function and muscle strength in certain parts of the leg or arm, and testing for pain in certain positions. A diagnostic test such as a CT scan or MRI scan can be used to detect anatomical lesions in the spine. Further, a discogram can be performed. The present methods, which culminate in the implantation of the present device, can include a step of identifying a patient in need of treatment.

The present device can be sterilized and provided in a package to maintain sterility or that can, as packaged, be sterilized. The device can be made in a variety of sizes to accommodate different individuals in need of treatment. Further, different components can be manufactured in varying sizes and selected by the surgeon for combination to accommodate the individual in need of treatment. For example, the arm 160, and the supporting member 110 of the device can be manufactured in different sizes.

The device can be implanted into a subject in need thereof by a surgical procedure through a posterior approach (from the back of the subject). Compared to an anterior approach (from the front of a subject), this surgical procedure is more simple, rapid and less invasive. The implantation can occur without removal of any bone, muscle, or ligament.

In some embodiments, the device has two extendable and rotatable arms. When implanting the device, the extendable arms can be folded and positioned to facilitate implantation. Once the device is at its intended position, the arms can be extended and rotated to stabilize the device relative to the spinous processes.

In some embodiments, the device has two extendable and non-rotatable arms. When implanting the device the extendable arms can be folded to facilitate implantation. Once the device is at its intended position, the arm can be extended to stabilize the device relative to the spinous processes.

In some embodiments, the device has one extendable and rotatable arm. When implanting the device, the extendable arm can be folded and positioned to facilitate implantation. Once the device is at its intended position, the arm can be extended and rotated to stabilize the device relative to the spinous processes.

In some embodiments, the device has one extendable and non-rotatable arm. When implanting the device the arm can be positioned to facilitate implantation. Once the device is at its intended position, the arms can be rotated to stabilize the device relative to the spinous processes.

In some embodiments, the supporting member 110 and the side members 130a and 130b can be contiguous with one another, with no visible joints or seams.

In some embodiments, one or more members or components of the spinous stabilization device can be separated from and joined with one or more other members or components of the spinous stabilization device. In these embodiments, any member or component that can be separated from and joined with another member or component is described as "detachable". Any member or component can be contiguous with another, with no visible joints or seams, to form a "contiguous unit". In some embodiments, a contiguous unit can be detachable from one or more other members or components of the spinous stabilization device. For example (as shown in FIG. 5), side members 130a and 130b are contiguous with each other as part of contiguous unit 200 which is detachable from supporting member 110. A first detachable member or component of the spinous stabilization device may be joined to a second detachable member or component of the spinous stabilization device by any method or device so long as the method or device connects the first member or component to the second member or component. For example, a fastener can be used. The fastener can be a hook-type fastener, a clip, or a fastener containing male-female connectors. The first or second member or component can be configured to receive a fastener that is not initially an integral part of the device. For example, the first or second member or component can include holes or hooks through which, or by which, a fastener (e.g., a clip, suture, screw, or nut and bolt) can be secured to join the first and second member or component. The holes and/or hooks can vary in number (e.g., there may be one, two, three or more holes and/or hooks in each of the first or second member or component). The fastener may be an integral part of the member or component. For example (as shown in FIG.

5), contiguous unit 200 can be joined to supporting member 100 using male-female connectors that are integral to the structures of contiguous unit 200 and supporting member 100.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus comprising:
   a supporting member defining an upper surface and a lower surface, the upper and lower surfaces being of a shape and dimension to support spinous processes of two adjacent vertebrae of a vertebral column;
   a left side member having a proximal end and a distal end, the proximal end of the left side member being connected to a left side of the supporting member,
   a right side member having a proximal end and a distal end, the proximal end of the right side member being connected to a right side of the supporting member,
   wherein the left side member and the right side member are configured such that the distal end of the left side member and the distal end of the right side member can be fastened to each other when the apparatus is implanted between two adjacent spinous processes.

2. The apparatus of claim 1, further comprising
   a first arm coupled to an exterior side of the left side member, and
   a second arm coupled to an exterior side of the right side member.

3. The apparatus of claim 2, wherein the first arm is rotatable relative to the left side member.

4. The apparatus of claim 2, wherein one or both arms has a length that is extendable.

5. The apparatus of claim 2, wherein one or both arms are X-shaped.

6. The apparatus of claim 2, wherein one or both arms are wing-shaped.

7. The apparatus of claim 2, wherein one or both arms are conical-shaped.

8. The apparatus of claim 1, wherein the upper surface defines an arc.

9. The apparatus of claim 8, wherein the upper surface is U-shaped.

10. The apparatus of claim 8, wherein the upper surface is semicircle-shaped.

11. The apparatus of claim 8, wherein the lower surface is semicircle-shaped.

12. The apparatus of claim 1, wherein the lower surface defines an arc.

13. The apparatus of claim 12, wherein the lower surface is U-shaped.

14. The apparatus of claim 1, wherein the distal end of the left side member and the distal end of the right side member are fastened by hook-typed fastener.

15. The apparatus of claim 1, wherein the distal end of the left side member and the distal end of the right side member are fastened by a fastener containing a male connector and a female connector.

16. The apparatus of claim 1, wherein the apparatus is made of one or more types of biocompatible material.

17. The apparatus of claim 1, wherein the supporting member, the left side member, and the right side member form an integral unit.

18. A method of maintaining an anatomical height of adjacent spinous processes, comprising implanting the interspinous stabilization device of claim 1 between two adjacent spinous processes in a subject.

19. The method of claim 18, wherein the interspinous stabilization device is implanted by a posterior approach.

* * * * *